United States Patent [19]

Roff et al.

[11] Patent Number: 5,308,310
[45] Date of Patent: May 3, 1994

[54] PLETHYSMOGRAPH SYSTEM AND AIR-TIGHT SEALING ASSEMBLY THEREFOR

[75] Inventors: Terence M. Roff, Westwood, N.J.; Jerome B. Korten, New York, N.Y.

[73] Assignee: Vitaltrends Technology, Inc., New York, N.Y.

[21] Appl. No.: 931,714

[22] Filed: Aug. 18, 1992

[51] Int. Cl.⁵ ............................................. A61G 10/00
[52] U.S. Cl. ..................................................... 600/21
[58] Field of Search ................................... 600/21-22; 128/716, 202.012, 202.013

[56] References Cited

U.S. PATENT DOCUMENTS

| | | |
|---|---|---|
| 2,708,927 | 5/1955 | Dixon et al. |
| 3,789,853 | 2/1974 | Reinhard . |
| 3,889,670 | 6/1975 | Loveland et al. |
| 4,031,312 | 6/1977 | Coleman et al. |
| 4,089,571 | 5/1978 | Landy ............................. 600/21 |
| 4,361,137 | 11/1982 | Grosholz ........................ 600/22 |
| 4,671,297 | 6/1987 | Schulze, Jr. |
| 4,926,844 | 5/1990 | Lindley ........................... 600/21 |
| 4,972,842 | 11/1990 | Korten et al. |

FOREIGN PATENT DOCUMENTS

2557457 6/1977 Fed. Rep. of Germany .

Primary Examiner—Lee S. Cohen
Assistant Examiner—J. P. Lacyk
Attorney, Agent, or Firm—Hoffmann & Baron

[57] ABSTRACT

A plethysmograph system is provided for monitoring neonates in an intensive care setting. The system includes a base and a pivotably attached lid which together define an air-tight chamber in which an infant can be positioned. The lid is mounted to the base so that it may be rotated between a position in which it is seated upon the base to a storage position directly beneath the base. The lid includes a peripheral gasket which is made from hollow tubing. The base also includes a gasket which is engageable by the lid gasket. The base gasket is made from substantially softer material than the lid gasket. First and second sealing members are mounted to the base and lid, respectively, for providing an air-tight seal about IV tubes and the like, extending from outside the chamber to an infant within the chamber. Each sealing member includes a number of channels for receiving such tubes. Each channel includes a set of parallel, deformable walls extending completely across the channels. The walls are deformed by the tubes within the channels, thereby assisting in providing air-tight seals about the tubes. The deformable walls of the respective sealing members engage each other when no tube is present within a channel, thereby providing an air-tight seal when the lid is closed. A hinge assembly connects the lid to the base, and includes a friction clutch assembly for preventing the lid from moving under its own weight.

26 Claims, 13 Drawing Sheets

PLETHYSMOGRAPH SYSTEM AND AIR-TIGHT SEALING ASSEMBLY THEREFOR

BACKGROUND OF THE INVENTION

1. Field of the Invention

The field of the invention relates to plethysmograph systems, and seals for providing an air-tight closure between the cover and lid of a plethysmograph and for sealing off tubes and/or cables extending into the airtight chamber of such an apparatus.

2. Brief Description of the Prior Art

Plethysmograph systems have been developed for monitoring the pulmonary functions of both infants and adults. A pair of such systems are described in U.S. Pat. Nos. 4,671,297 and 4,972,842, the latter of which is incorporated by reference herein.

The flow through a plethysmograph is used for monitoring patient ventilation, usually in ICU (intensive care unit) settings. The plethysmograph includes a sealed chamber in which a patient is placed. The tidal volume of air inspired and expired through the ventilator tubing causes volume displacements from the plethysmograph to the atmosphere through a flow resistive leak. The rise and fall of pressure within the plethysmograph can then be related to the amount of air displaced with each breath, allowing the measurement of tidal volumes.

A plethysmograph is usually configured as a box that has a hinged wall or lid with a rubber gasket or seal around the perimeter thereof. The preferred arrangement in patient settings is for the plethysmograph to be constructed in a "clamshell" configuration where the top and the bottom of the box are not of equal depth. This way, when the plethysmograph is opened, the patient is not recessed or difficult to access but is right at the surface of the opening.

As described in U.S. Pat. No. 4,972,842, the flow through a plethysmograph system for monitoring neonates in the intensive care setting requires an airtight seal. Typically, the patient is subject to supportive therapies that include intravenous administration of drugs, plasma or various electrolytes. While it is possible to disconnect IV tubes and reconnect them across bulkhead fittings that feed through an airtight seal, this approach is flawed for many reasons. Firstly, the possibility of introducing air bubbles, violating sterility or clotting blood are reasons not to break and reconnect an IV tube. Furthermore, to require this type of connection every time the patient is introduced to or removed from the plethysmograph would be a strong disincentive to the use of the flow through plethysmograph in an ICU setting.

SUMMARY OF THE INVENTION

It is an object of the invention to provide a plethysmograph which includes a substantially airtight chamber.

It is another object of the invention to provide a sealing assembly which allows the passage of IV tubes, chest tubes and patient cables through the sealing assembly such that the patient can be introduced to the plethysmograph without disconnecting such tubes and cables.

A still further object of the invention is to provide a plethysmograph which allows easy access to the patient, and the ability to position the patient in a number of different positions.

In accordance with these and other objects of the invention, a plethysmograph is provided which includes a base, a lid which is positionable upon the base, the base and lid being constructed so as to define a substantially airtight chamber when the lid is positioned upon the base. A sealing assembly is provided for allowing a patient to be placed in the chamber without first disconnecting IV tubes and the like. The sealing assembly includes first and second sealing members. At least one of the sealing members includes a channel including a plurality of resilient, deformable walls. The first and second sealing members are engageable with each other, preferably upon engagement of the lid with the base. Upon such engagement, a tube or cable passing between the members deforms the resilient, deformable walls, which thereby form a substantially airtight seal about the tube or cable. Preferably, both sealing members include a plurality of deformable walls. The walls extend across the longitudinal axis of the tube or cable, and preferably run substantially parallel to each other. Notches are preferably defined within the sealing members to facilitate mounting tubes or cables thereto and for providing improved sealing capability. The notches are preferably semicircular, and are oriented such that cables or tubes therein are directed across the deformable walls.

A sealing arrangement is also provided for sealing the engaging surfaces of the base and lid. The arrangement includes first and second sealing portions, one of which is secured to the base and the other to the lid. One of the sealing portions may simply include an elongate resilient strip, such as a closed cell silicone sponge strip. The other sealing portion includes an elongate, deformable hollow tube. The base and lid are designed such that the hollow tube engages the resilient strip when the lid is mounted to the base. This arrangement provides a substantially airtight seal.

The plethysmograph according to the invention is designed to facilitate access to the patient. The apparatus accordingly includes a base, a lid, and a hinge assembly connecting the lid to the base. The hinge assembly allows the lid to be moved from a first position in which it engages the base to a second position which it is located substantially directly beneath the base. A physician's access to the base, which supports the patient, will accordingly be unimpeded. Means are provided for preventing the lid from closing of its own weight.

BRIEF DESCRIPTION OF THE DRAWINGS

FIG. 6b is a sectional view taken along line 6b—6b of FIG. 6a;

DETAILED DESCRIPTION OF THE INVENTION

A plethysmograph is provided for monitoring the respiration of a patient. The plethysmograph 10 shown in the figures is specifically designed for monitoring infants, but many of the features thereof may be adapted for maintaining an air-tight chamber and monitoring the conditions of larger patients.

Figure 1:
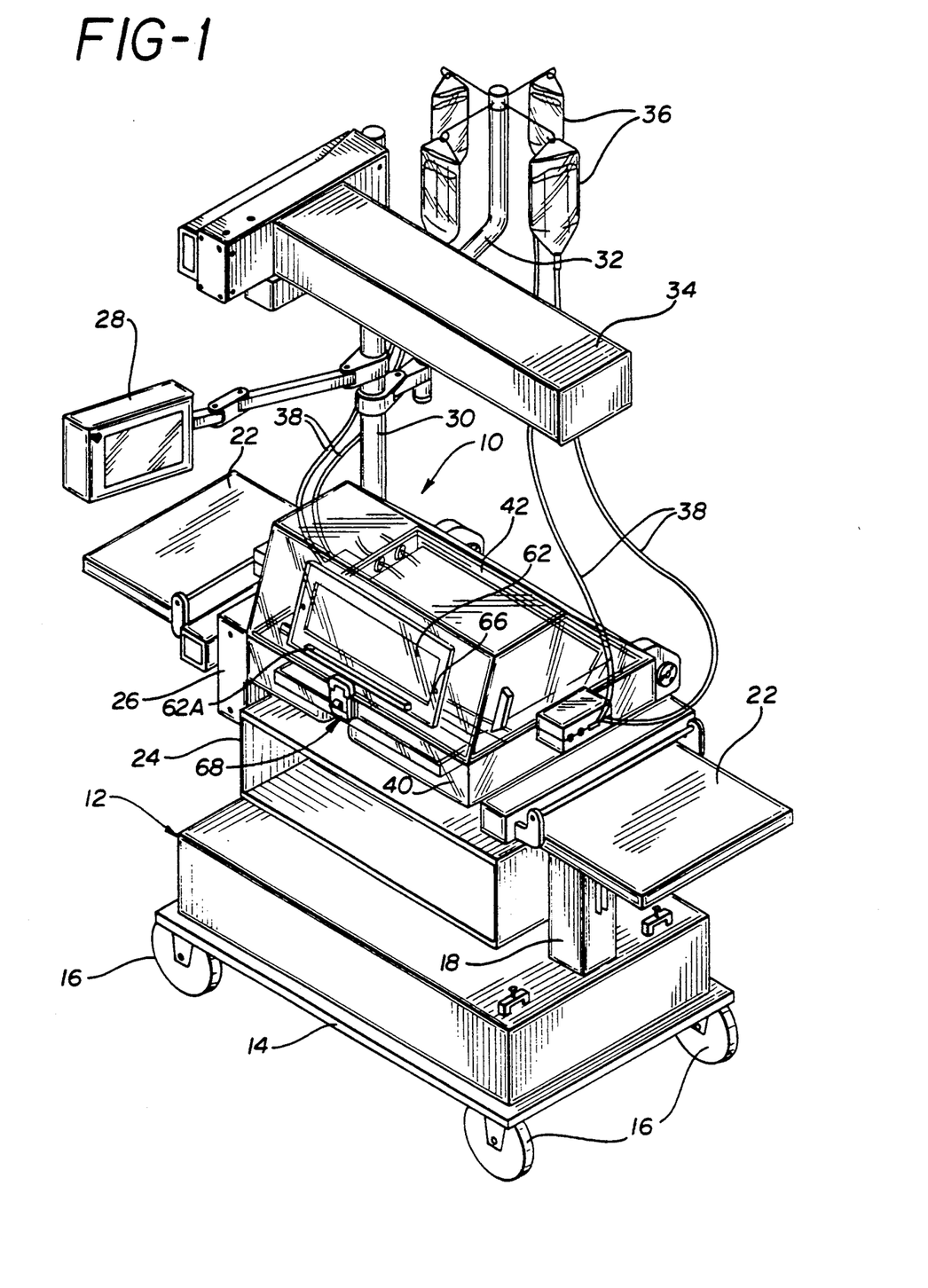
FIG. 1 is a top perspective view of a plethysmograph according to the invention and associated equipment used therewith.
Figure 3:
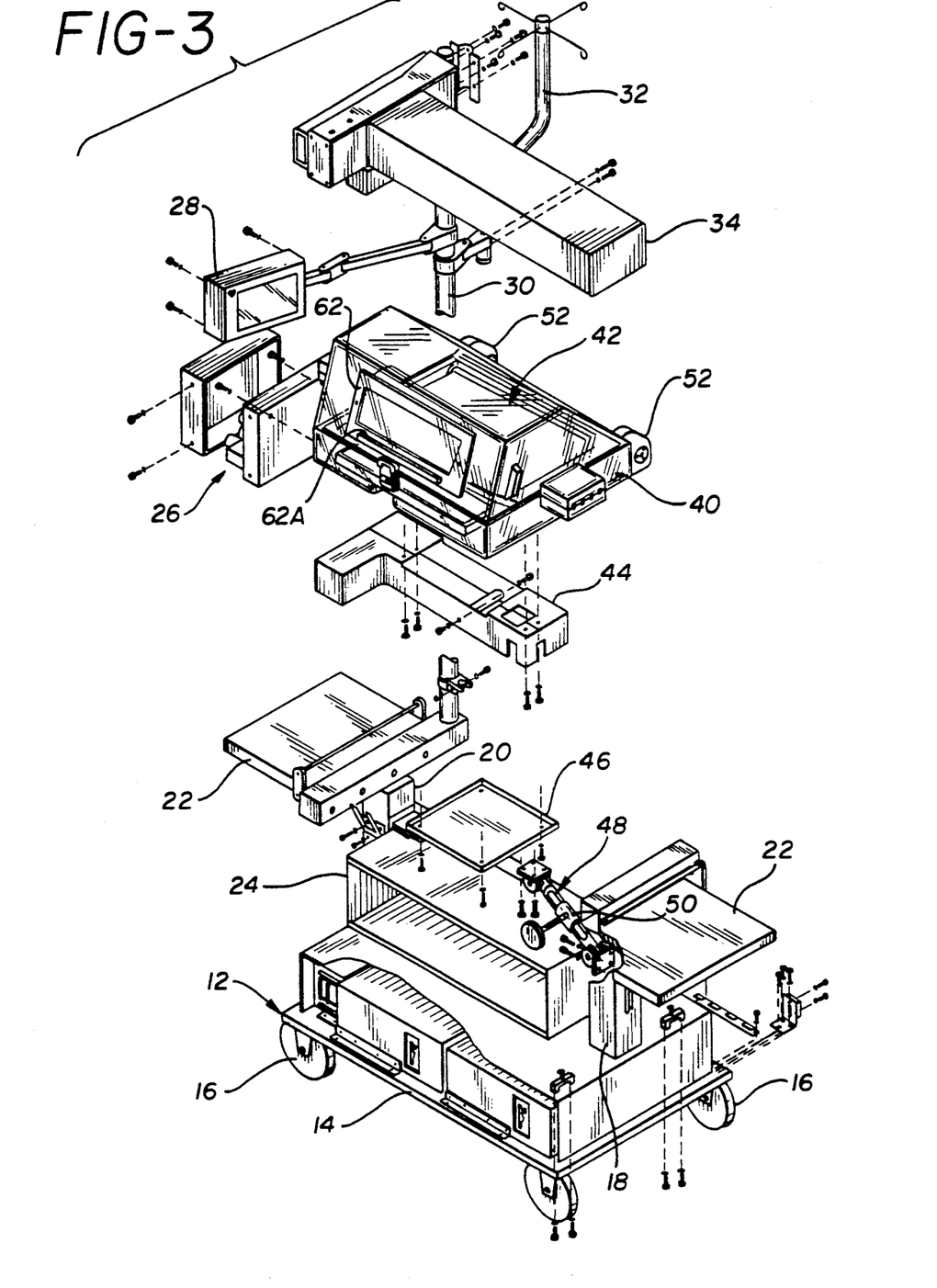
FIG. 3 is an exploded, perspective view thereof.

FIG. 1 shows a plethysmograph 10 and much of the equipment which is employed therewith. The plethysmograph is mounted to a cart 12. The cart includes a base portion 14 having casters 16 secured thereto. A pair of columns 18, 20 extend upwardly from the base of the cart. The latter column is shown in FIG. 3. Each column supports a pivotably mounted tray 22 movable between the horizontal position shown in FIG. 1 and a vertical storage position. A storage compartment 24 is mounted between the columns 18, 20.

A pressure pulse source, pneumotachometer and other components for sensing and measuring the flow of air are mounted as a unit 26 to a wall of the plethysmograph. These components are thoroughly described in U.S. Pat. No. 4,972,842, together with the electronics for calibrating and operating the apparatus. As this patent is incorporated in its entirety by reference herein, a detailed discussion of the mode of operation of the plethysmograph 10 is unnecessary. Like the apparatus discussed in U.S. Pat. No. 4,972,842, a video display terminal 28 is employed for displaying values corresponding to total tidal volume, volume due to infant respiratory efforts, and volume due to mechanical ventilation.

The video display terminal 28 is supported by a column 30 which is also used to support an IV pole 32 and a radiant heater 34. Bags 36 of nutrients, medication or other materials are supported by the IV pole, and IV tubes 38 extend therefrom and into the plethysmograph 10 for supplying the patient (not shown).

The plethysmograph 10 includes a base 40 and a lid 42 which is pivotably mounted to the base. The base 40 is secured to a support 44 which is, in turn, mounted to a platform 46 as shown in FIG. 3. A platform mounting assembly 48, including a telescoping member 50, is provided for supporting the platform 46. The telescoping member may be adjusted to support the platform in a number of positions. This allows the base 40 to be moved between a horizontal position and a Trendelenburg position.

Figure 4:
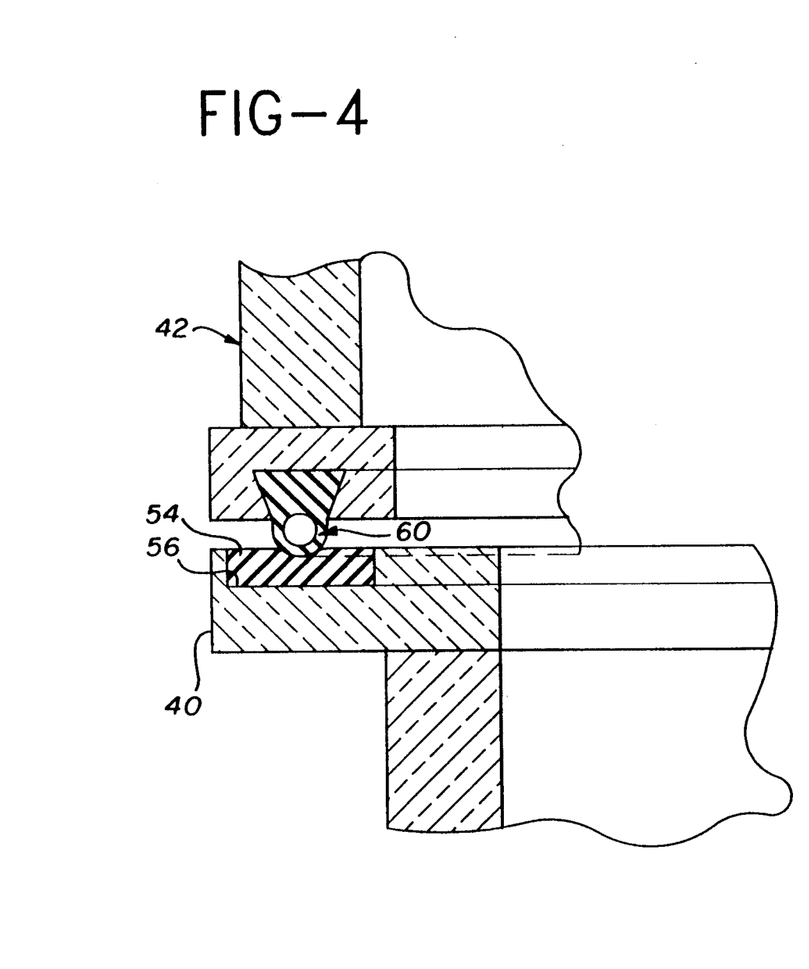
FIG. 4 is a sectional view of the edge portions of the lid and base of the plethysmograph in sealing engagement.
Figure 5:
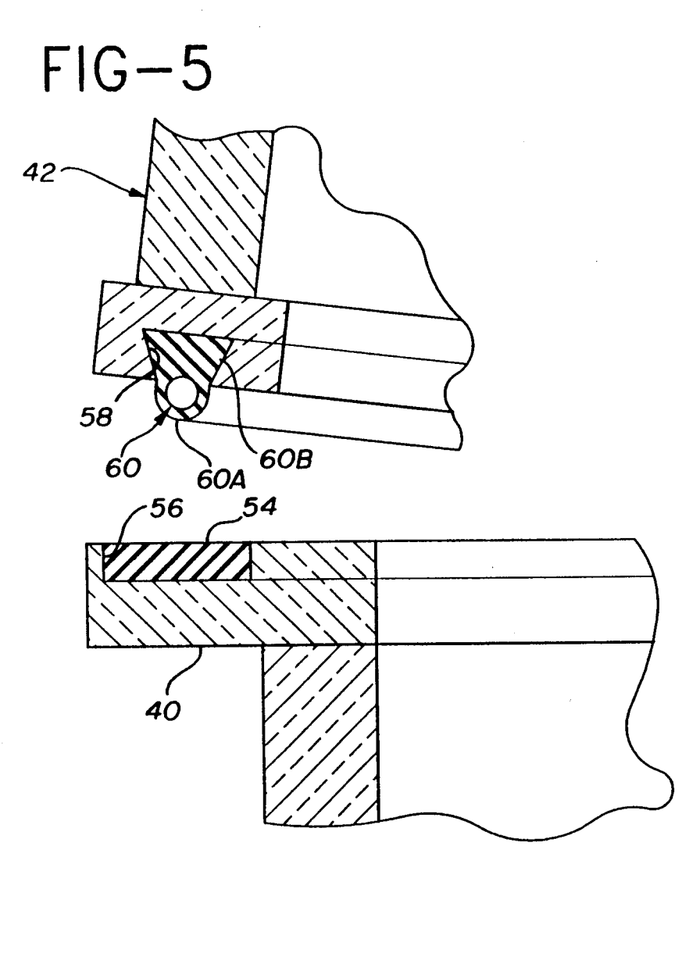
FIG. 5 is similar to FIG. 4 and shows the edge portions of the lid and base as disengaged from each other.

It is important to maintain a reliable air-tight seal between the lid and the base of the plethysmograph 10. The peripheral edges of the lid and base are accordingly provided with gaskets or seals as best shown in FIGS. 4 and 5. The hinge assemblies 52 which couple the lid to the base allow the lid to contact a replaceable gasket 54 secured to the base with substantially equal pressure about the entire contact area.

A recess 56 is provided within the base. The base gasket 54 is positioned within the recess 56 such that its top surface is substantially flat and coplanar with the top surface of the base. Both the base gasket and associated recess are preferably rectangular in cross section, as shown in the figures.

A substantially trapezoidal recess 58 is provided within the lower edge of the lid. A gasket 60 including a tube-like portion 60A and a trapezoidal portion 60B is secured to the lid, the trapezoidal portion being positioned within the recess 58. The tube-like portion provides a generally arcuate contact surface which deforms the flat surface of the base gasket upon contact therewith. An adhesive may be used to secure each gasket to the base and lid, respectively. While both gaskets are made from an elastomeric material, the base gasket 54 is preferably made from softer material than the lid gasket 60. The base gasket is preferably made from a closed cell silicone sponge strip having a width of about one quarter of an inch and a thickness of about one eighth of an inch. The base gasket has good memory characteristics and readily returns to its original shape upon disengagement from the lid gasket.

The lid gasket is preferably extruded from a resilient material such as silicone rubber, and is substantially more resistant to deformation than the base gasket. The base gasket accordingly deforms to a much greater extent than the lid gasket when the lid is closed. It has been found that the physical structures of the gaskets and the difference in hardness (durometer) between them compensates for surface irregularities and provides a good, air-tight seal.

The lid 42, like the base 40, is preferably made from a transparent material. The lid end panels 42A and the base may, for example, be constructed from 0.375 inch thick acrylic sheets assembled with solvent bonding using dichloromethane. The remaining portions of the lid can be made from the same material having a quarter inch thickness.

Figure 2:
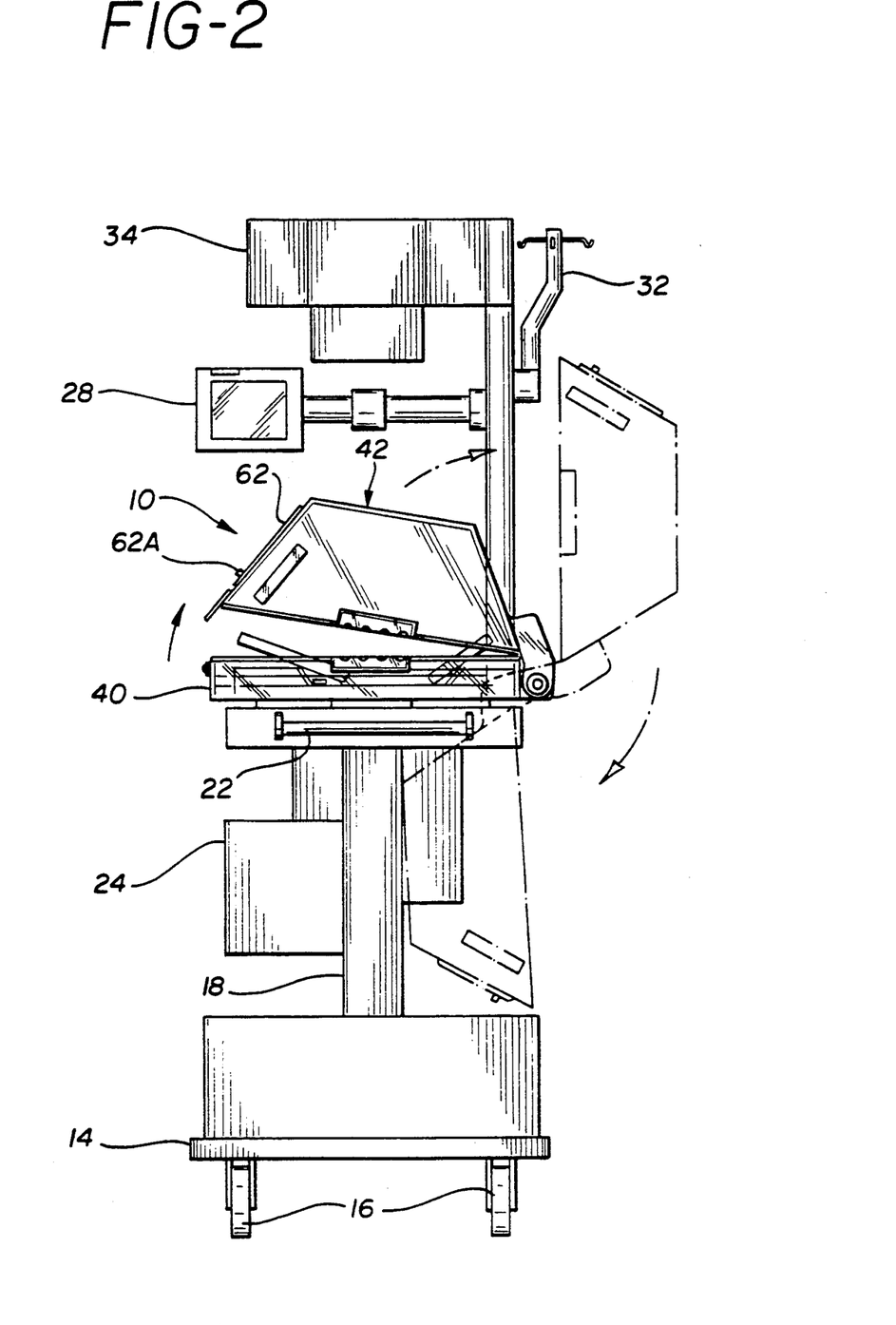
FIG. 2 is a front elevation view thereof showing how the lid may be positioned with respect to the base of the plethysmograph.

Access to the chamber defined by the base and lid should be easy for the attending nurse or physician. An infant access hatch is accordingly provided in the front panel 42B of the lid. The hatch is ordinarily closed by a clear, acrylic cover 62 which is secured to the front panel by acrylic hinges 64. An air-tight seal is formed between the cover 62 and panel 42B by an EPDM (ethylene-propylene diene monomer) sponge gasket adhered to the peripheral edges of the cover. Magnets 66 are secured to both the cover and panel 42B to insure that the air-tight seal is maintained. An elongate handle 62A extends from the cover 62 to facilitate disengagement of the magnets. If greater access to the chamber is desired, the lid may be moved about the hinge assemblies 52 as shown in FIG. 2. The lid may advantageously be moved about an arc of approximately 270° so that it may be stored directly beneath the base 40. It accordingly will not interfere with a person administering treatment to an infant supported by the base.

Figure 6A:
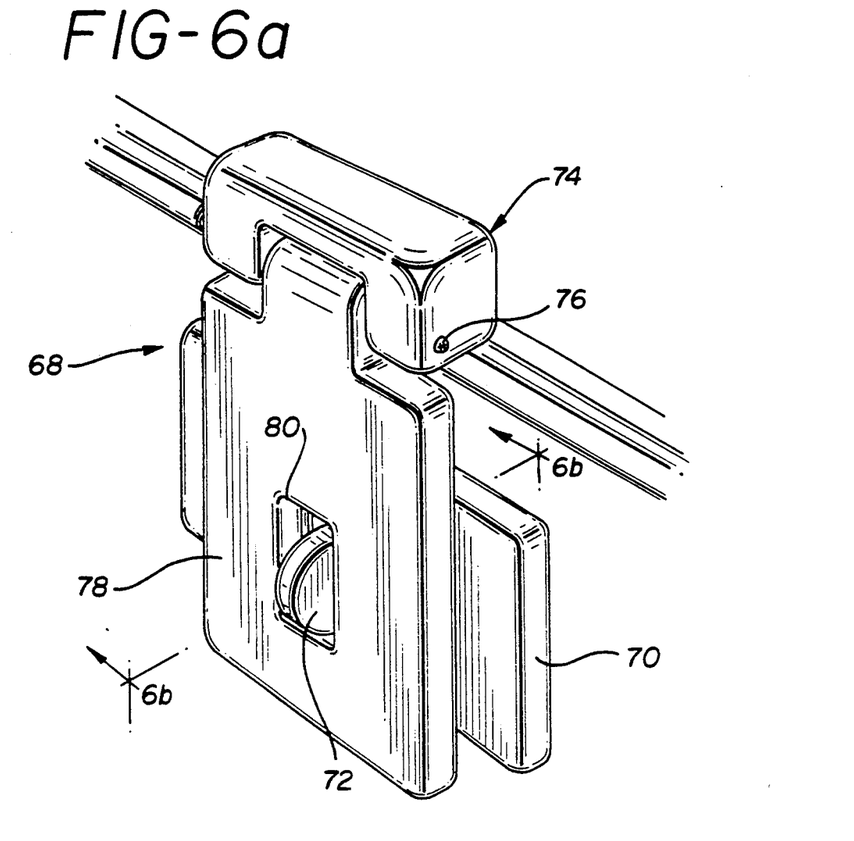
FIG. 6a is a top perspective view of a locking assembly for locking the lid to the base of the plethysmograph.
Figure 6B:
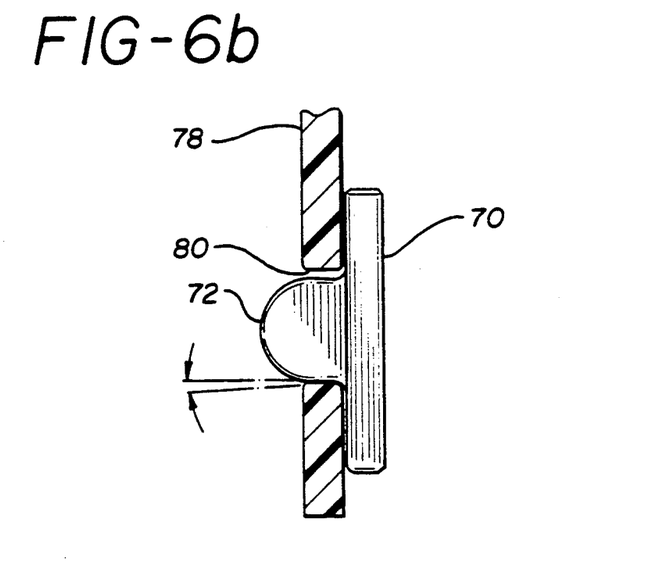

In order to prevent the lid from being inadvertently dislodged from the base, a latch assembly 68 as shown in FIGS. 6a and 6b is provided. The latch assembly includes a plate 70 secured to the base 40. A projection 72 having an arcuate end extends perpendicularly from the plate. A housing 74 is secured to the front panel 42B of the lid 42 just beneath the hatch opening. The housing includes a pivot pin 76 to which a plate 78 is secured. The plate 78 includes an opening 80 which receives the projection such that the projection bears against the plate surface defining the lower boundary of the opening 80. The lid 42 accordingly tends to be pulled down slightly upon movement of the latch plate 78 into the latching position, thereby promoting an air-tight seal between the lid and the base.

Figure 7:
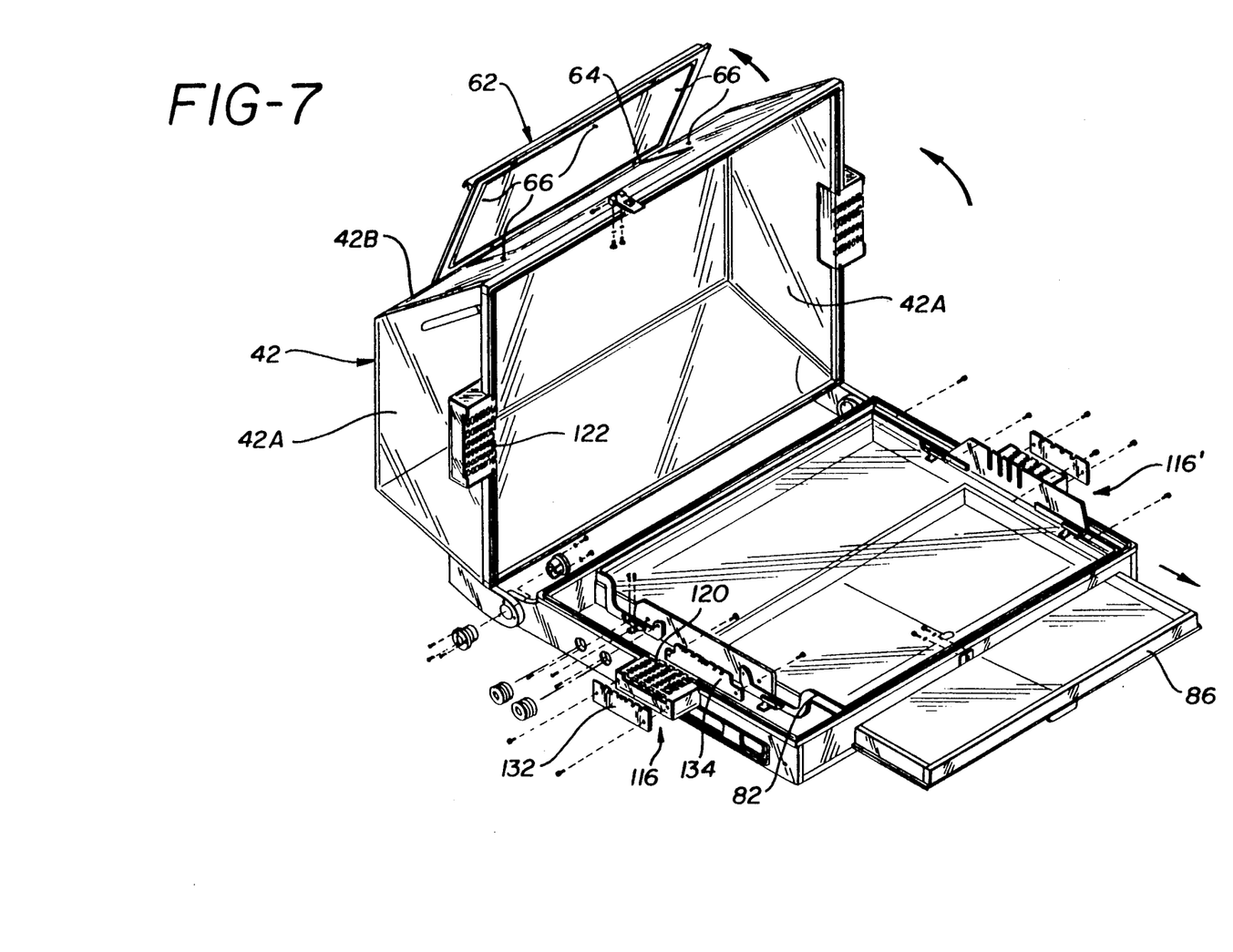
FIG. 7 is a front perspective, partially exploded view of the plethysmograph according to the invention with the lid in the partially open position.
Figure 8:
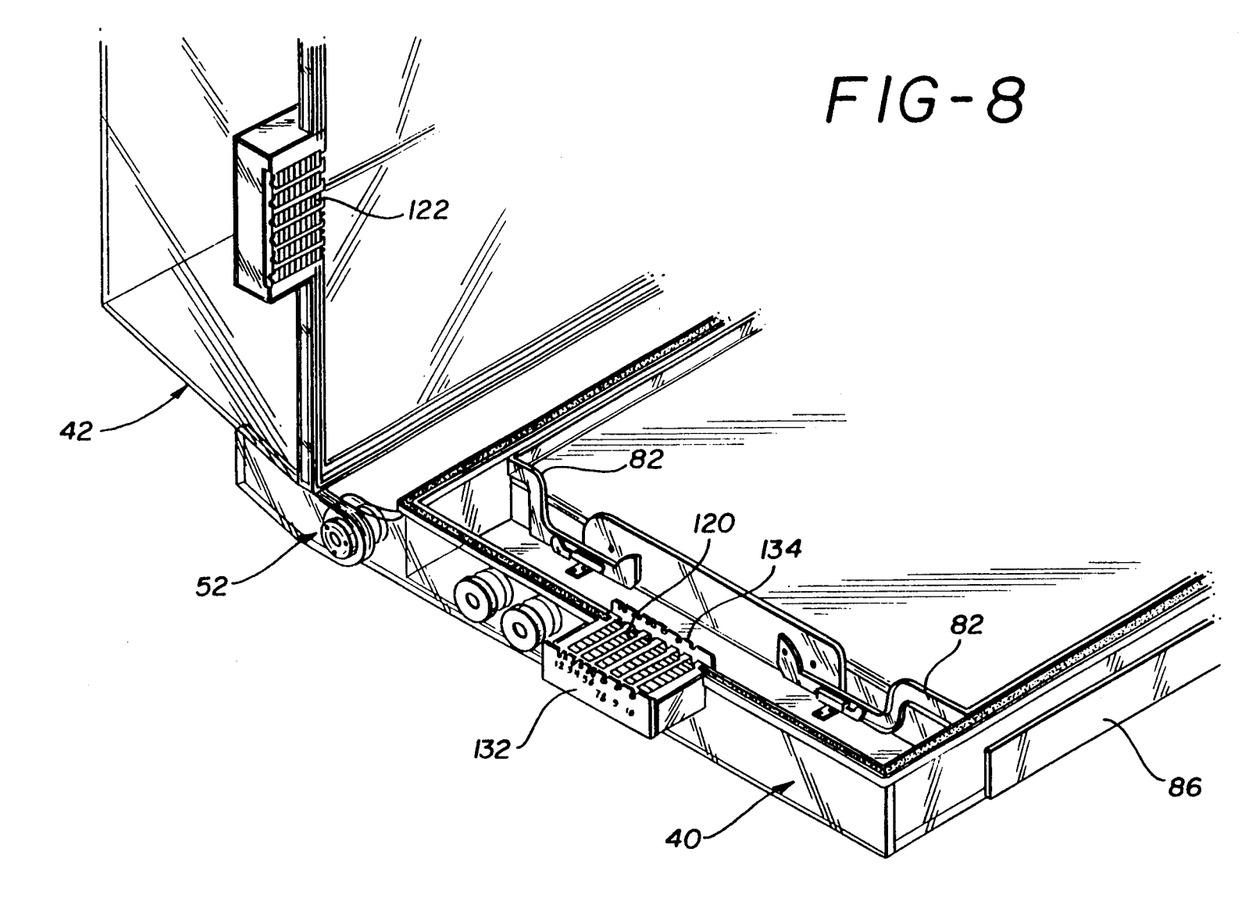
FIG. 8 is an enlarged perspective view of a lateral edge portion thereof.
Figure 9:
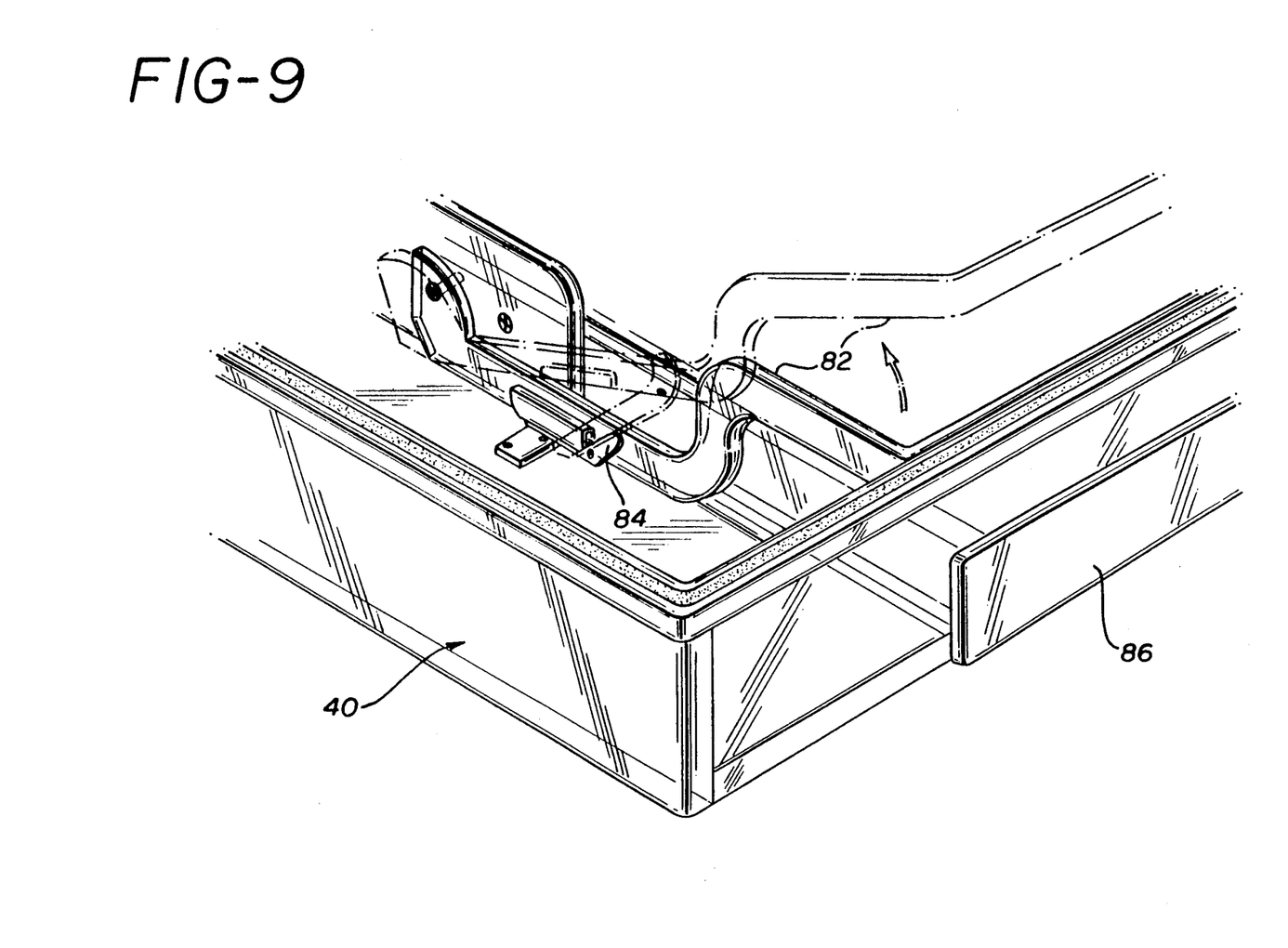
FIG. 9 is an enlarged perspective view of a portion of the base thereof showing a portion of a retaining rail.

Referring to FIGS. 7-9, a pair of retaining members 82 are pivotably mounted to the base 40. When in the raised position, as shown in phantom lines in FIG. 9, the retaining members prevent an infant from rolling off the base. A support 84 is provided for maintaining such retaining member in the raised position once moved thereto.

A slot is defined in the front panel of the base of the plethysmograph. A tray 86 is positioned within the base, and may be pulled out through the slot as shown in FIG. 7. The tray is adapted for positioning an x-ray plate or the like beneath the base so that diagnostic tests may be run without having to remove the patient from the plethysmograph.

As discussed above, providing easy access to the patient is an important consideration in the design of the plethysmograph according to the invention. Safety is, of course, another important objective. The lid 42 is accordingly designed to be moved with respect to the base 40 to allow full access to the patient. As the attending nurse or physician may wish to position the lid in a vertical orientation, as shown in FIG. 7, or below the base as shown in phantom lines in FIG. 2, it is important that the lid stay in the desired position. The hinge assemblies 52 are accordingly designed so that the lid is movable without undue effort to any desired position, but will not move simply under the force of gravity. The risk of injury to the nurse and patient due to a falling lid is accordingly eliminated.

Figure 10:
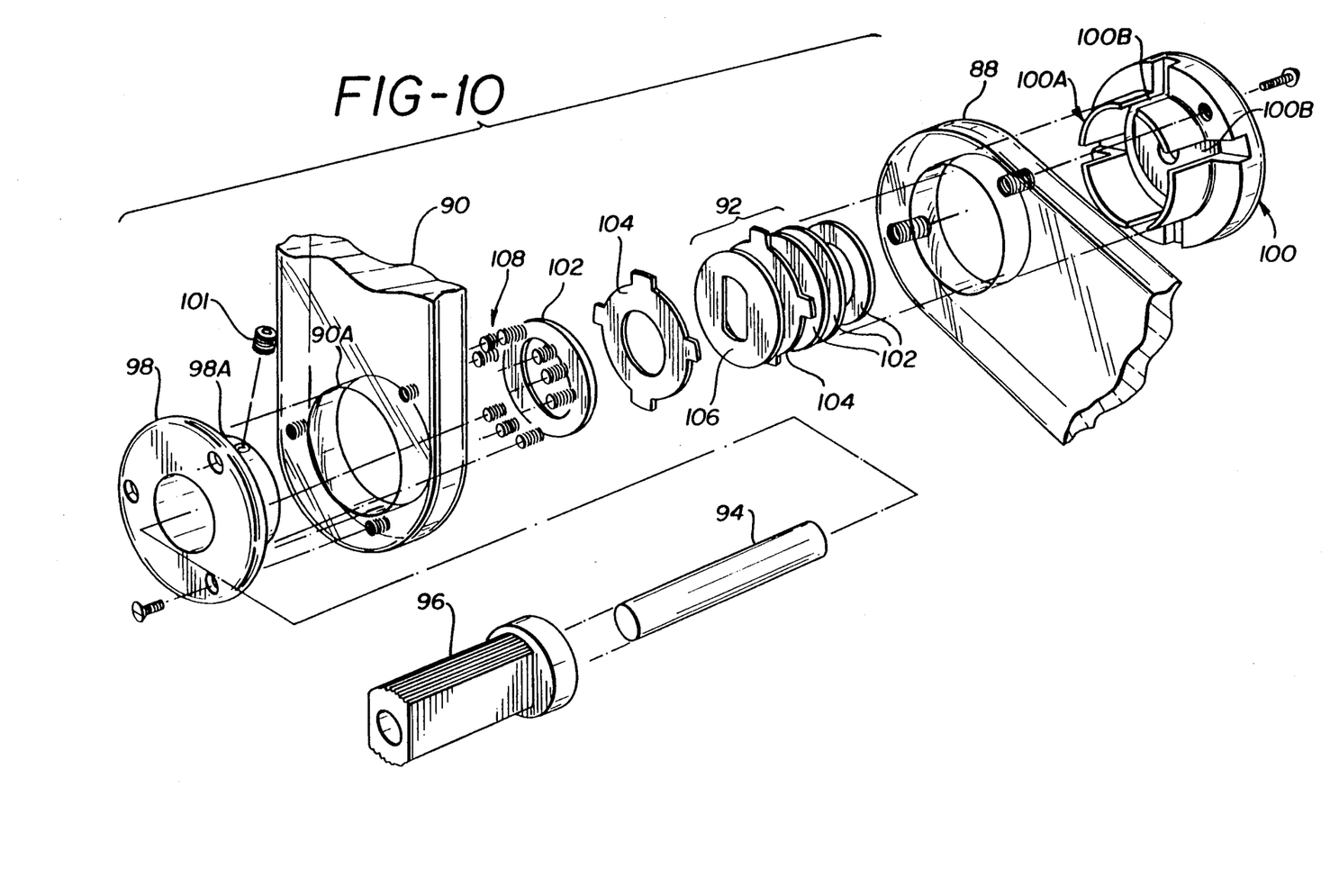
FIG. 10 is an exploded perspective view of a hinge assembly for connecting the lid to the base.

Referring to FIGS. 8 and 10, each hinge assembly 52 is comprised of an arm 88 extending rearwardly from the base 40, an arm 90 extending from a side panel of the lid 42, a friction clutch assembly 92, and a pivot pin 94 about which the arms 88,90 may rotate. The friction clutch assembly is designed to slip at a predetermined torque. It includes a sleeve 96 which receives the pivot pin. The sleeve includes a generally rectangular shaft. A first end support 98 is secured to the lid arm 90, and a second end support 100 is secured to the base arm 88. The second end support includes a cylindrical projection 100A having four equally spaced slots 100B therein. The first end support also includes a cylindrical projection 98A having a radial opening for receiving lock screw 101. The lid arm 90 includes an opening 90A which receives the cylindrical projection 98A of the first end support while the base arm 80 includes an opening 88A which receives the cylindrical projection 100A of the second end support. A set of spacers 102 and stationary plates 104 are positioned within the cylindrical projection 100A. The plates 104 each include four projections which are positioned within the slots 100B. A circular plate 106 having a generally rectangular opening is positioned between the stationary plates 104. The plate is rotatable upon rotation of the sleeve 96 about the pivot pin. Such rotation is impeded by the friction between the plates 104,106. A set of coil springs 108 bears against one of the spacers 102 for resiliently urging the plates and spacers together.

Figure 11:
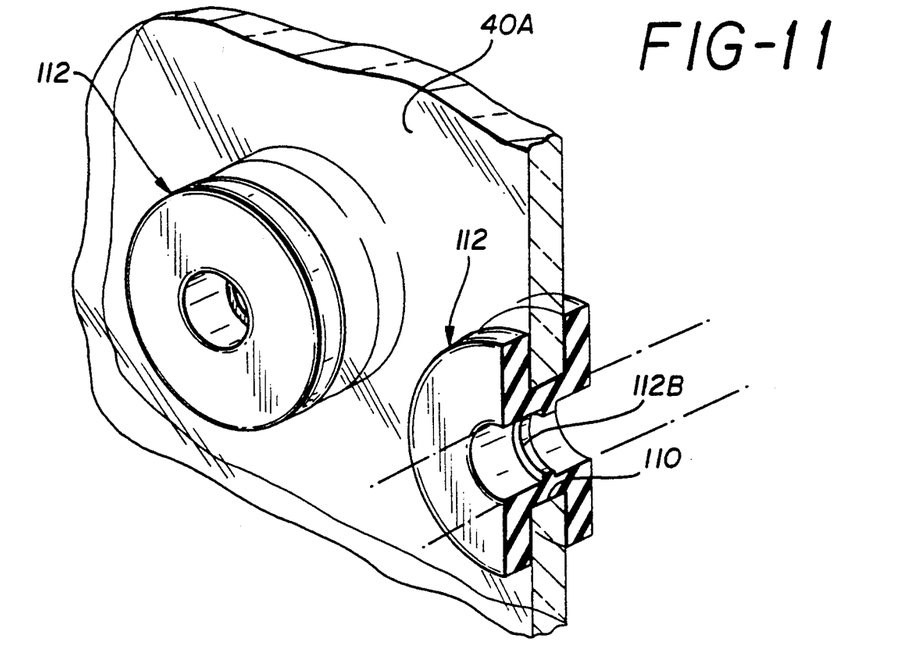
FIG. 11 is a partially sectional, perspective view of a pair of ventilator tube bushings extending through a wall of the base.
Figure 12:
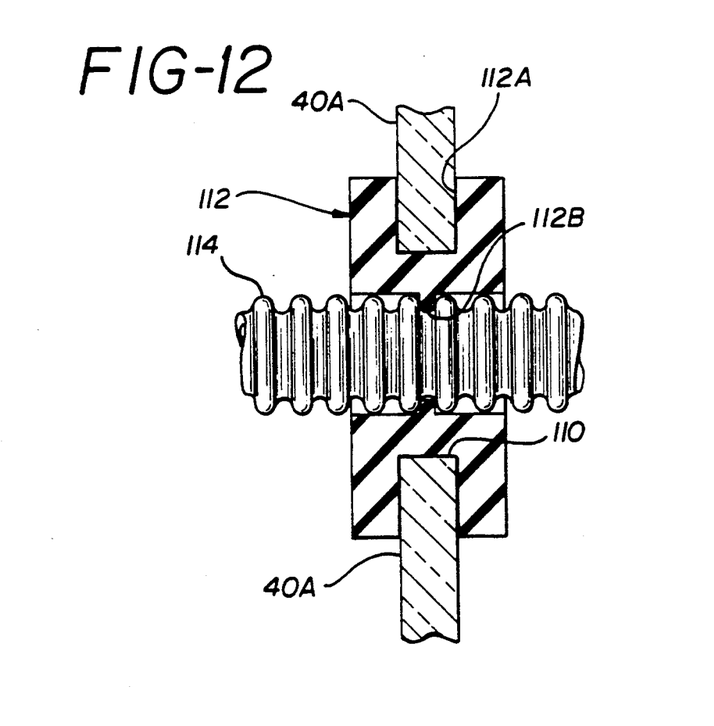
FIG. 12 is an enlarged sectional view taken through one of the bushings and including a ventilator tube therein.
Figure 13:
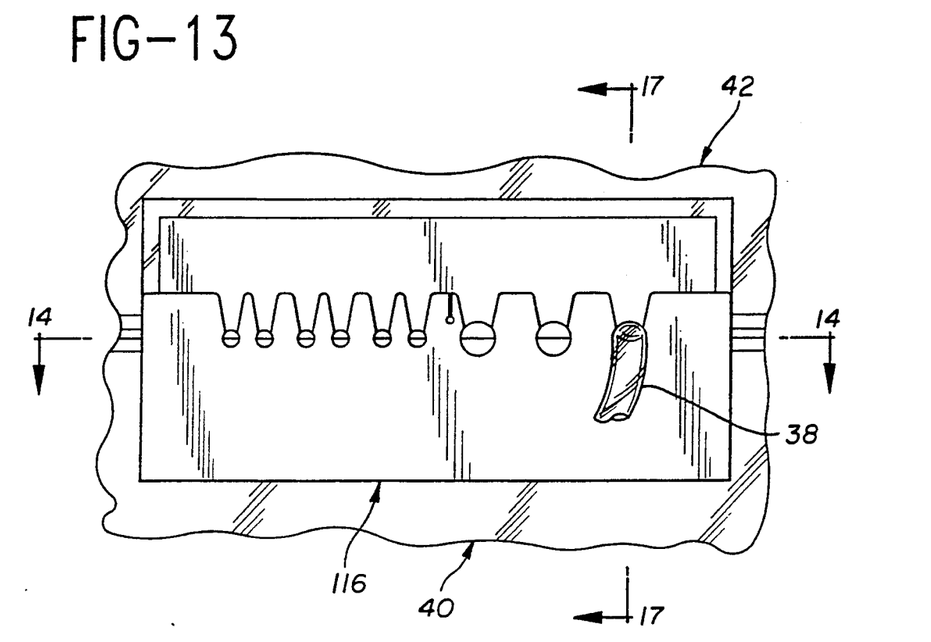
FIG. 13 is a front elevation view of a cable/tube sealing assembly according to the invention.

As discussed above, it is important to maintain an airtight chamber with a controlled, single flow resistive leak. This allows pressure transients that are proportional to air flow through the resistive leak to be measured. Such flows are due to the expansion and contraction of the infant's chest during inspiration and exhalation. The ports for admitting the corrugated supply and exhaust tubes must accordingly provide an air-tight seal with these tubes. Referring to FIGS. 11-12, a pair of ports 110 are provided within an end panel 40A of the base 40. A pair of resilient bushings 112 made from silicone or other elastomeric material are secured to the end panel 40A. Each bushing 112 includes an exterior slot 112A which sealingly engages the end panel 40A. An annular rib 112B extends radially inwardly from the inner wall of the bushing. The rib fits between the corrugations of a ventilator tube 114 as shown in FIG. 12. The bushings 112 provide substantially air-tight seals with the ventilator tubes while allowing the tubes to be removed without undue difficulty.

Referring now to FIGS. 7, 8 and 13-18, a sealing assembly 116, 116' is provided at each side of the plethysmograph for allowing the air-tight introduction of IV tubes 38 and monitoring cables (not shown). One sealing assembly 116 includes a first sealing member 120 secured to the base 40 and a second sealing member 122 secured to the lid 42. The other sealing assembly 116' also includes such first and second sealing members, which may or may not be identical to their counterparts at the opposite side of the apparatus.

Figure 14:
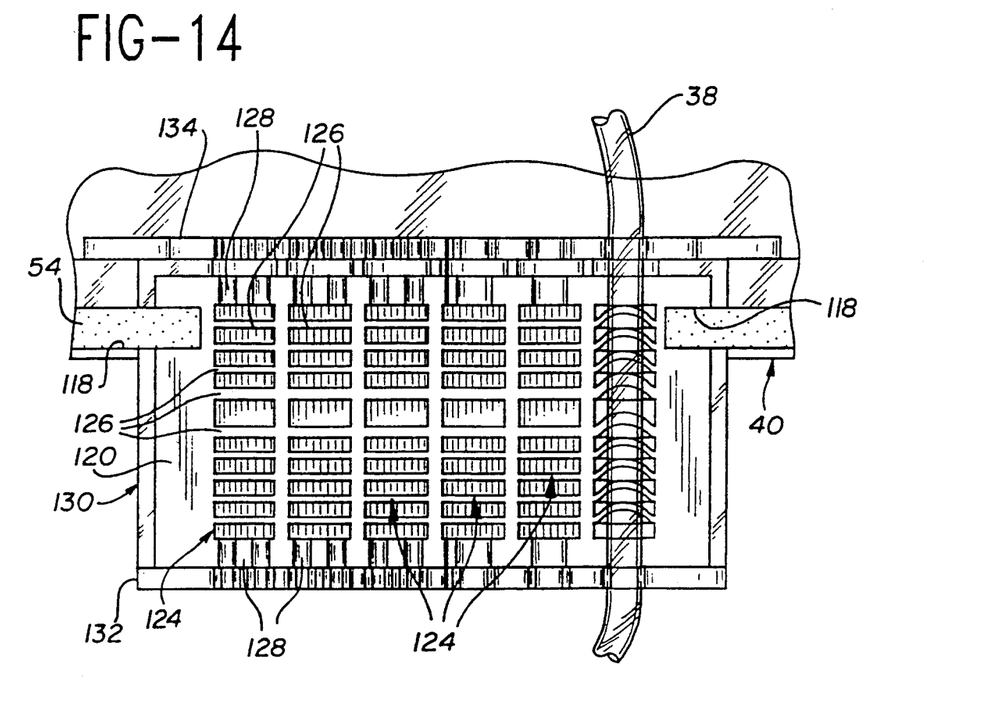
FIG. 14 is a top plan view of a sealing member secured to the base of the plethysmograph and a tube in engagement therewith.
Figure 15:
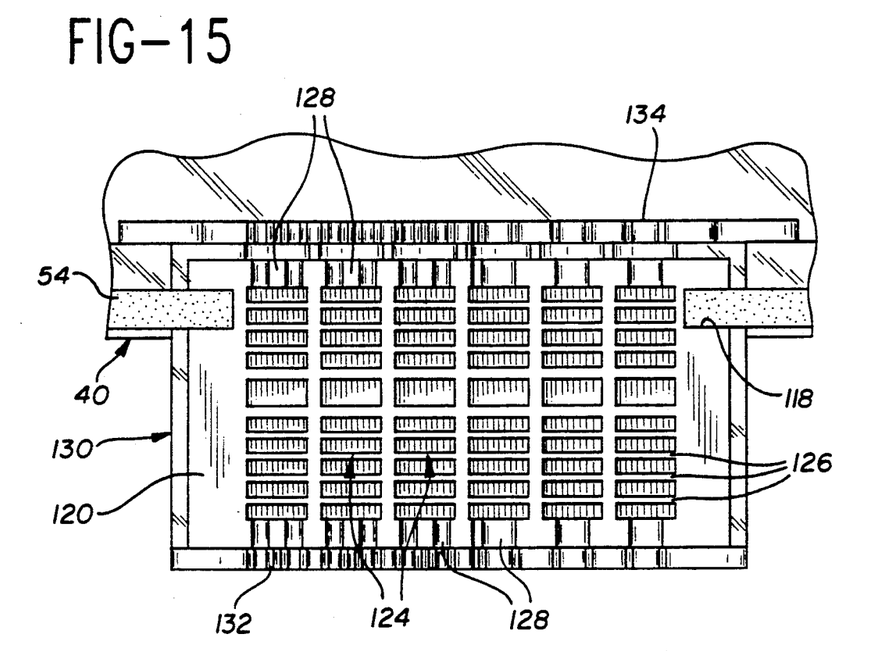
FIG. 15 is similar to FIG. 14 without a tube.

As shown in FIGS. 14 and 15, the first sealing member 120 has a substantially rectangular configuration. It is made from a soft, elastomeric material which will readily deform as described below when a tube is positioned within the sealing assembly. A preferred material is silicone rubber. Three zones of different hardness are preferably provided in each sealing member 120,122. Referring to FIG. 15, zones A and C are the softest, each having a hardness of about 11 Shore-A. The middle zone B is of medium softness, with a durometer hardness of about 30 Shore-A.

The first sealing member 120 includes a plurality of substantially parallel channels 124. Each channel may have a depth between about 0.2 and 0.4 inches. The preferred depth is proportional to the diameter of the tube or cable to be accommodated. A plurality of resilient, deformable walls 126 extend laterally across each channel in zone B of the sealing member. These walls are preferably parallel to each other and equal in height. The top surfaces of the walls are also preferably coplanar with the remainder of the top surface of the sealing member. Each wall may have a thickness of about 0.07 inches, while the distance between walls may be about 0.12 inches. A slightly larger wall thickness, and a slighter greater distance between walls, may be utilized near the central portion of the sealing member. A scalloped, semicylindrical channel 128 is provided at each end of the substantially parallel channels. The sizes of the semicylindrical channels 128 are proportional to the sizes of the tubes or cables intended to pass therethrough. The radius of each channel may accordingly range from about 0.07 inches to 0.17 inches for typical applications.

The first sealing member 120 is positioned within a housing 130 such that at least the top surface thereof is exposed. The top surface of the sealing member is preferably substantially coplanar with or slightly above the top surface of the housing 130. First and second hard durometer (about 60 Shore-A) plates 132, 134 extend across the sealing member, one inside the plethysmograph and the other outside thereof. Each plate includes a number of notches, as shown in FIGS. 7 and 8. The notches aid in the alignment of the IV tubes and cables. The base gasket 54 extends into the housing 130 and the sealing member 120. The sealing member preferably includes a pair of notches 118, each having about the same dimensions as the portion of the base gasket which is positioned therein.

Figure 16:
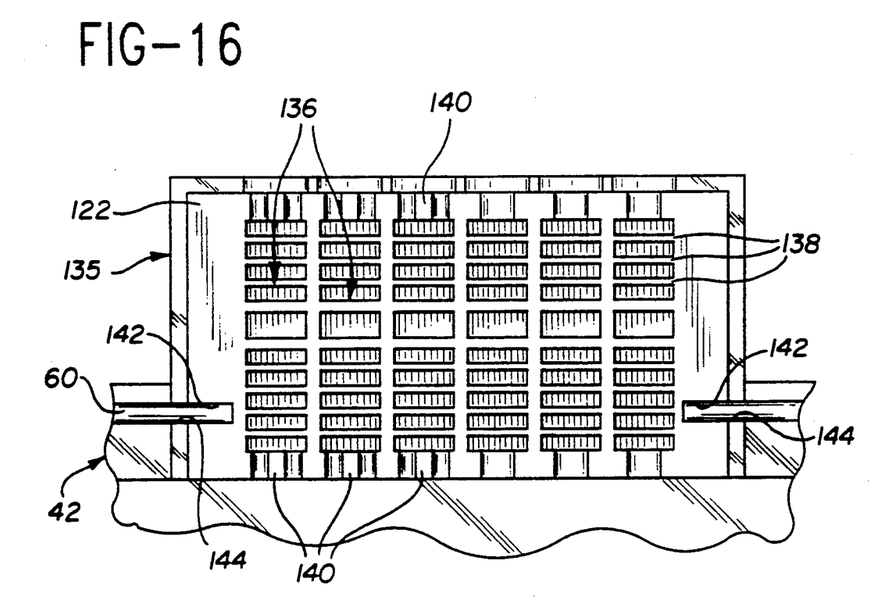
FIG. 16 is a top plan view of a sealing member secured to the lid of the plethysmograph.
Figure 17:
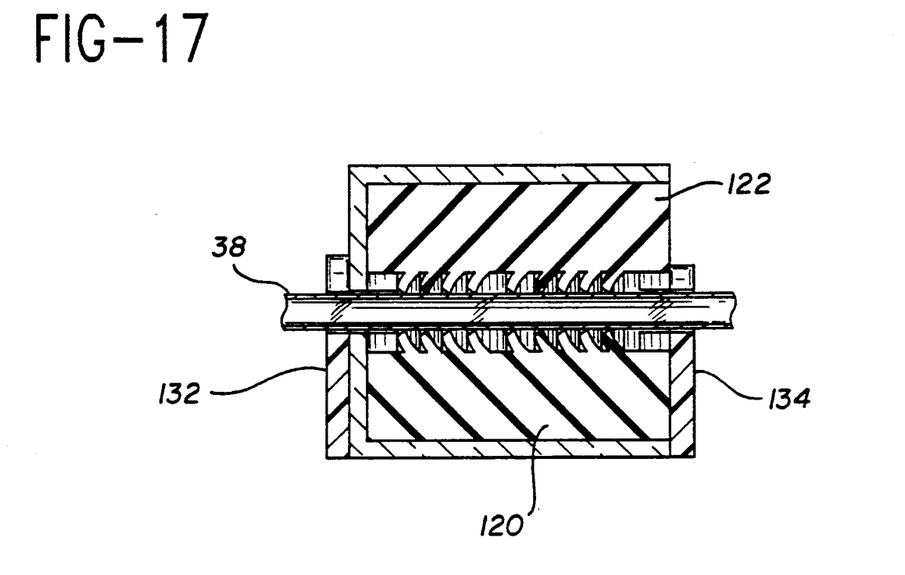
FIG. 17 is a sectional view showing a tube extending through the sealing assembly of FIG. 13.
Figure 18:
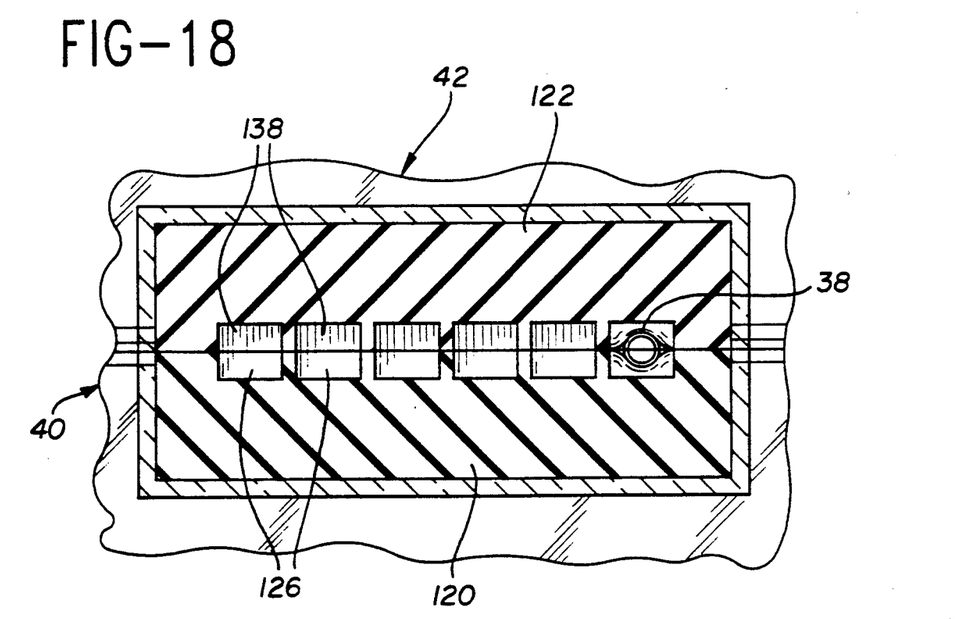
FIG. 18 is a sectional view of the sealing assembly of FIG. 13 taken through a plane perpendicular to the plane through which the view shown in FIG. 17 is taken.

The second sealing member 122 is substantially identical to the first sealing member 120. It is encased within a housing 135 so that the bottom surface thereof is exposed, as shown in FIG. 16. The channels 136 and resilient, deformable walls 138 thereof are aligned with the corresponding channels 124 and walls 126 of the first sealing member 120 when the lid is closed. As shown in FIGS. 17 and 18, the walls 126, 138 collapse about an IV tube when pressed over it, thereby contributing to the formation of an air-tight seal. The semicylindrical channels 128, 140 also aid in providing such a seal as the surfaces thereof engage the cable or tube. The channels having no tube or cable extending therethrough are also sealed as the outer wall surfaces of the resilient, deformable walls 126, 138 engage each other.

A pair of notches 142 are provided within the second sealing member 122. These notches conform to the configuration of the lid gasket 60. Two ends of the lid gasket are positioned within the notches 142 such that the gasket is substantially flush with the exposed surface of the second sealing member. The housing 134 also includes a pair of notches 144 through which the lid gasket extends.

The features of the plethysmograph according to the invention provide safety, accessibility and reliability. The lid 42 may be safely opened without the danger of it falling under its own weight. It can also be moved directly beneath the base 40 to allow the patient to be accessed from either side of the apparatus.

The construction of the bushings 112, sealing assemblies 116, 116' and gaskets 54, 60 insure that the chamber defined by the lid 42 and base 40 will be substantially air-tight. The only leakage of air will accordingly occur under controlled conditions, which allows the patient's pulmonary functions to be closely monitored. The sealing assemblies are advantageously designed to provide air-tight seals whether tubes or cables extend through them or not. They also allow the plethysmograph to be closed with an air-tight seal about any tubes or cables therein by simply closing the lid. No additional steps are required. The lid and base gaskets are designed to provide an air-tight seal upon closure of the lid. The hinge assembly is designed such that, when closed, the lid rests with even force about the perimeter of the base. The relatively hard, though elastomeric, lid gasket 60 accordingly deforms the relatively soft base gasket 54 so that air cannot escape therebetween.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A plethysmograph system comprising:
a base;
a lid, the base and the lid defining a substantially air-tight chamber when the lid is positioned upon the base;
a sealing assembly for providing an air-tight seal about a tube, said sealing assembly including first and second sealing members, one of said sealing members being secured to said base, the other of said sealing members being secured to said lid, at least one of said sealing members including a channel including a plurality of resilient walls extending across said channel, said channel including means for directing a tube into said chamber;
said first and second sealing members engaging each other when said lid is positioned upon said base, said walls being deformed when a tube extends through said channel and said first and second sealing members are engaged with each other, said walls engaging the other of said sealing members when no tube extends through said channel, said sealing assembly providing a substantially air-tight seal when said first and second sealing members are engaged with each other whether or not a tube extending through said channel, and
means for introducing air into said chamber.

2. A plethysmograph system as described in claim 1, wherein each of said first and second sealing members includes a channel including a plurality of resilient, walls extending across the channel.

3. A plethysmograph system as described in claim 2, wherein each of said first and second sealing members includes a plurality of channels, each of said channels including a plurality of resilient walls extending across the channel.

4. A plethysmograph system as described in claim 3, wherein the channels in each sealing member are substantially parallel to each other and the walls extending across each channel are substantially parallel to each other.

5. A plethysmograph system as described in claim 3, said base includes a first housing extending laterally therefrom, said lid includes a second housing extending laterally therefrom, said first sealing member being mounted within said first housing such that the channels therein are exposed, said second sealing member being mounted within said second housing such that the channels therein are exposed.

6. A plethysmograph system as described in claim 5, including a hinge assembly connecting said base and said lid, said first and second sealing members being in engagement and the channels in said respective sealing members being aligned with each other when said lid is moved about said hinge assembly to a closed position, said sealing members being disengaged when said lid is moved about said hinge assembly to an open position.

7. A plethysmograph system as described in claim 5, including a rigid plate secured to each housing, each plate including a plurality of notches aligned with the channels of each respective sealing member.

8. A plethysmograph system as described in claim 2, wherein the channel in each sealing member includes a semicylindrical portion.

9. A plethysmograph system as described in claim 2, wherein the channel in each sealing member includes substantially semicylindrical end portions, said resilient walls being located between said end portions.

10. A plethysmograph system as described in claim 1, wherein said base includes a first peripheral gasket and said lid includes a second peripheral gasket, said first gasket forming a substantially air-tight seal with said second gasket when said lid is positioned upon said base, a portion of said first gasket extending into one of said sealing members, and a portion of said second gasket extending into the other of said sealing members.

11. A plethysmograph comprising:
a base;
a lid mounted to said base, said base and said lid defining a chamber when said lid is positioned upon said base;
a first gasket comprised of an elongate strip of a soft material;
a second gasket comprised of a hollow elongate tube a resilient material which is of harder durometer than the material comprising said first gasket, said elongate tube including a generally arcuate surface portion which engages said first gasket when said lid is positioned upon said base;
means for introducing air into said chamber;
one of said first and second gaskets being mounted to said base and extending substantially peripherally thereabout;
the other of said first and second gaskets being mounted to said lid and extending substantially peripherally thereabout,
whereby said second gasket engages substantially the entire length of said first gasket when said lid is positioned upon said base, thereby deforming said first gasket and providing a substantially air-tight seal.

12. A plethysmograph as described in claim 11, wherein said first gasket is secured to said base and said second gasket is secured to said lid.

13. A plethysmograph as described in claim 11, wherein said first gasket includes a substantially flat surface.

14. A plethysmograph as described in claim 11, wherein said lid includes an elongate recess, said second gasket being at least partially positioned within said recess such that said generally arcuate surface portion extends outside said recess.

15. A plethysmograph as described in claim 14, wherein said recess within said lid is at least partially trapezoidal in cross section, said second gasket including a base portion substantially conforming in dimension to said recess and positioned within said recess.

16. A plethysmograph as described in claim 11, wherein said means for introducing air into said chamber include a port within said base, a bushing positioned within said port, said bushing including a passage extending therethrough and an annular rib extending radially inwardly into said passage.

17. A plethysmograph as described in claim 11, including means for heating said chamber.

18. A plethysmograph comprising:
a base;
a lid mounted to said base, said base and said lid defining a substantially air-tight chamber when said lid is positioned substantially horizontally upon said base;
means for introducing air into said chamber;
supporting means for supporting said base;
a storage space defined by said supporting means directly beneath said base;
a hinge assembly connecting said base and said lid such that said lid can be pivoted about said hinge assembly through an arc of at least about 270°, whereby said lid is pivotable about said hinge assembly from a substantially horizontal position upon said base to a substantially vertical position within said storage space directly beneath said base.

19. A plethysmograph as described in claim 18, including means for preventing said lid from moving about said arc under the force of gravity.

20. A plethysmograph as described in claim 19, wherein said means for preventing said lid from moving includes a friction clutch assembly incorporated within said hinge assembly.

21. A plethysmograph as described in claim 20, wherein said hinge assembly includes a pivot pin connecting said base and said lid, a sleeve rotatably mounted to said pivot pin, a first plate mounted to said sleeve and rotatable therewith, a second plate, a third plate, said first plate being positioned between and in frictional engagement with said second and third plates, said second and third plates resisting rotation of said first plate with respect thereto.

22. A plethysmograph as described in claim 18, wherein said lid includes a front panel, an opening within said front panel, and a cover pivotably mounted to said front panel and covering said opening.

23. A plethysmograph as described in claim 18, including a first sealing member secured to said base and a second sealing member secured to said lid, said first and second sealing members including means for providing a substantially air-tight seal about a tube extending between said first and second sealing members and into said chamber.

24. A plethysmograph as described in claim 23, wherein each of said sealing members includes a plurality of channels, each of said channels including a plurality of soft, resilient walls extending across said channels.

25. A plethysmograph as described in claim 18, including a first gasket mounted to and extending peripherally about said base, a second gasket mounted to and extending peripherally about said lid, said second gasket including a hollow, tubular portion having an arcuate surface which engages said first gasket when said lid is positioned upon said base.

26. A plethysmograph as described in claim 18 including a first arm extending from said base, a second arm extending from said lid, said hinge assembly including a pivot pin extending through said first and second arms.

* * * * *